(12) United States Patent
Cragg et al.

(10) Patent No.: US 6,440,153 B2
(45) Date of Patent: *Aug. 27, 2002

(54) DEVICE AND METHOD FOR FACILITATING HEMOSTASIS OF A BIOPSY TRACT

(75) Inventors: Andrew H. Cragg, Edina, MN (US); Rodney Brenneman, San Juan Capistrano; Mark Ashby, Laguna Niguel, both of CA (US)

(73) Assignee: Sub-Q, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/953,395

(22) Filed: Sep. 14, 2001

Related U.S. Application Data

(63) Continuation of application No. 09/613,059, filed on Jul. 10, 2000, which is a continuation of application No. 09/247,880, filed on Feb. 10, 1999, now Pat. No. 6,086,607, which is a continuation-in-part of application No. 09/071,670, filed on May 1, 1998, now Pat. No. 6,071,301.

(51) Int. Cl.[7] .......................... A61B 17/08; A61F 13/20
(52) U.S. Cl. .......................................... 606/213; 604/15
(58) Field of Search ................................ 606/213, 214; 604/263, 192, 265

(56) References Cited

U.S. PATENT DOCUMENTS

| | | |
|---|---|---|
| 581,235 A | 4/1897 | Kenyon |
| 1,578,517 A | 3/1926 | Hein |
| 2,086,580 A | 7/1937 | Shirley |
| 2,465,357 A | 3/1949 | Correll |
| 2,492,458 A | 12/1949 | Bering, Jr. |
| 2,507,244 A | 5/1950 | Correll |
| 2,558,395 A | 6/1951 | Studer |
| 2,597,011 A | 5/1952 | MacMasters et al. |
| 2,680,442 A | 6/1954 | Linzmayer |
| 2,761,446 A | 9/1956 | Reed |

(List continued on next page.)

FOREIGN PATENT DOCUMENTS

| | | |
|---|---|---|
| EP | 0032826 | 7/1981 |
| EP | 0476178 | 3/1992 |
| EP | 0482350 | 4/1992 |
| FR | 2641692 | 1/1990 |
| GB | 1509023 | 3/1975 |
| GB | 1569660 | 7/1977 |
| RU | 782814 | 1/1977 |
| RU | 1088709 | 2/1981 |
| WO | WO 96/08208 | 3/1996 |
| WO | WO 98/06346 | 2/1998 |
| WO | WO 99/66834 | 12/1999 |

OTHER PUBLICATIONS

Sigmund Silber, M.D., FACC, "Rapid Hemostasis of Arterial Puncture Sites with Collagen in Patients Undergoing Diagnostic and Interventional Cardiac Catheterization", Clinical Cardiology, vol. 20 (1997) pp. 981–992.

(List continued on next page.)

Primary Examiner—Howard Weiss
Assistant Examiner—(Vikki) Hoa B. Trinh
(74) Attorney, Agent, or Firm—Thelen Reid & Priest LLP; Robert E. Krebs

(57) ABSTRACT

A system including an adaptor and a syringe is used for facilitating hemostasis of a biopsy tract or other puncture wound by delivery of an absorbable sponge in a hydrated state into the wound. The adaptor includes a tapered lumen for hydrating and compressing the relatively large absorbable sponge for delivery through a relatively small cannula, such as a biopsy needle. The hydrated absorbable sponge is injected through the biopsy needle into the biopsy tract by fluid. Alternatively, the sponge may be delivered to the biopsy needle by injection of fluid and then delivered to the biopsy tract by a plunger or stylet. The implanted absorbable sponge facilitates hemostasis at the biopsy site or other puncture wound and minimizes the chance of internal bleeding. The absorbable sponge material is absorbed by the body over time.

18 Claims, 7 Drawing Sheets

U.S. PATENT DOCUMENTS

| | | |
|---|---|---|
| 2,814,294 A | 11/1957 | Figge |
| 2,824,092 A | 2/1958 | Thompson |
| 2,899,362 A | 8/1959 | Sieger, Jr. et al. |
| 3,157,524 A | 11/1964 | Artandi |
| 4,000,741 A | 1/1977 | Binard et al. |
| 4,323,072 A | 4/1982 | Rosenbluth et al. |
| 4,340,066 A | 7/1982 | Shah |
| 4,390,018 A | 6/1983 | Zulowski |
| 4,515,637 A | 5/1985 | Cioca |
| 4,587,969 A | 5/1986 | Gillis |
| 4,588,395 A | 5/1986 | Lemelson |
| 4,619,261 A | 10/1986 | Guerriero |
| 4,619,913 A | 10/1986 | Luck et al. |
| 4,645,488 A | 2/1987 | Matukas |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,850,960 A | 7/1989 | Grayzel |
| 4,852,568 A | 8/1989 | Kensey |
| 4,890,612 A | 1/1990 | Kensey |
| 4,900,303 A | 2/1990 | Lemelson |
| 4,929,246 A | 5/1990 | Sinofsky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,053,046 A | 10/1991 | Janese |
| 5,061,274 A | 10/1991 | Kensey |
| 5,080,655 A | 1/1992 | Haaga |
| 5,108,421 A | 4/1992 | Fowler |
| 5,163,904 A | 11/1992 | Lampropoulos et al. |
| 5,167,624 A | 12/1992 | Butler et al. |
| 5,192,300 A | 3/1993 | Fowler |
| 5,192,301 A | 3/1993 | Kamiya et al. |
| 5,195,988 A | 3/1993 | Haaga |
| 5,220,926 A | 6/1993 | Jones |
| 5,221,259 A | 6/1993 | Weldon et al. |
| 5,242,683 A | 9/1993 | Klaveness |
| 5,275,616 A | 1/1994 | Fowler |
| 5,310,407 A | 5/1994 | Casale |
| 5,325,857 A | 7/1994 | Nabai et al. |
| 5,334,216 A | 8/1994 | Vidal et al. |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammerslag |
| 5,388,588 A | 2/1995 | Nabai et al. |
| 5,391,183 A | 2/1995 | Janzen et al. |
| 5,419,765 A | 5/1995 | Weldon et al. |
| 5,431,639 A | 7/1995 | Shaw |
| 5,437,631 A | 8/1995 | Janzen |
| 5,467,780 A | 11/1995 | Nabai et al. |
| 5,478,352 A | 12/1995 | Fowler |
| 5,479,936 A * | 1/1996 | Nabai et al. ............ 128/898 X |
| 5,486,195 A | 1/1996 | Myers et al. |
| 5,522,850 A | 6/1996 | Yomtov et al. |
| 5,526,822 A | 6/1996 | Burbank et al. |
| 5,529,577 A | 6/1996 | Hammerslag |
| 5,540,715 A | 7/1996 | Katsaros et al. |
| 5,545,178 A | 8/1996 | Kensey et al. |
| 5,558,853 A | 9/1996 | Quay |
| 5,591,204 A | 1/1997 | Janzen et al. |
| 5,591,205 A | 1/1997 | Fowler |
| 5,601,602 A | 2/1997 | Fowler |
| 5,645,566 A | 7/1997 | Brenneman et al. |
| 5,649,547 A | 7/1997 | Ritchart et al. |
| 5,653,730 A | 8/1997 | Hammerslag |
| 5,665,107 A | 9/1997 | Hammerslag |
| 5,681,279 A | 10/1997 | Roper et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,830,130 A | 11/1998 | Janzen et al. |
| 5,868,762 A | 2/1999 | Cragg et al. |
| 5,902,310 A | 5/1999 | Foerster et al. |
| 5,984,950 A | 11/1999 | Cragg et al. |
| 6,027,471 A | 2/2000 | Fallon et al. |
| 6,027,482 A | 2/2000 | Imbert |
| 6,071,300 A | 6/2000 | Brenneman et al. |
| 6,071,301 A * | 6/2000 | Cragg et al. ............... 606/213 |
| 6,086,607 A | 7/2000 | Cragg et al. |
| 6,161,034 A | 12/2000 | Burbank et al. |
| 6,162,192 A | 12/2000 | Cragg et al. |
| 6,183,497 B1 | 2/2001 | Sing et al. |
| 6,200,328 B1 | 3/2001 | Cragg et al. |
| 6,315,753 B1 | 11/2001 | Cragg et al. |

OTHER PUBLICATIONS

Marc Zins, M.D., et al., "US–guided Percutaneous Liver Biopsy with Plugging of the Needle Track; A Prospective Study in 72 High–Risk Patients", Radiology, vol. 184 (1992) pp. 841–843.

David J. Allison, M.D., et al., "Percutaneous Liver Biopsy and Track Embolization with Steel Coils," Radiology, vol. 169 (1988) pp. 261–263.

Ferdinand Kiemeneij, M.D., et al., "Improved Anticoagulation Management After Palmaz Schatz Coronary Stent Implantation by Sealing the Arterial Puncture Site with a Vascular Hemostasis Device," Catherization and Cardiovascular Diagnosis, vol. 30 (1993) pp. 317–322.

J.P.M. Foran et al., "Early Mobilisation After Percutaneous Cardiac Catherisation Using Collagen Plug (VasoSeal) Haemostasis.", Br Heart, vol. 69 (1993) pp. 424–429.

Schrader, R., "Collagen Application", Catherization and Cardiovascular Diagnosis, (1992) pp. 298–302.

J.S.R. Gibbs, "Femoral Arterial Hemostasis,", Journal of Interventional Cardiology, vol. 5 (1992) pp. 85–88.

W.G. Kussmaul, "Rapid Arterial Hemostasis," Journal of the American College of Cardiology, vol. 25 (1995) pp. 1685–1692.

Timothy A. Sanborn, M.D., et al., "A Multicenter Randomized Trial Comparing a Percutaneous Collagen Hemostasis Device With Conventional Manual Compression After Diagnostic Angiography and Angioplasty," Journal of American College of Cardiology, vol. 22, No. 5 (1993) pp. 1273–1279.

Pharmacia & Upjohn Manufacturer Brochure, "*Gelfoam Sterile Sponge, Sterile Powder, and Sterile Film*," (May 1997) pp. 1–34.

* cited by examiner

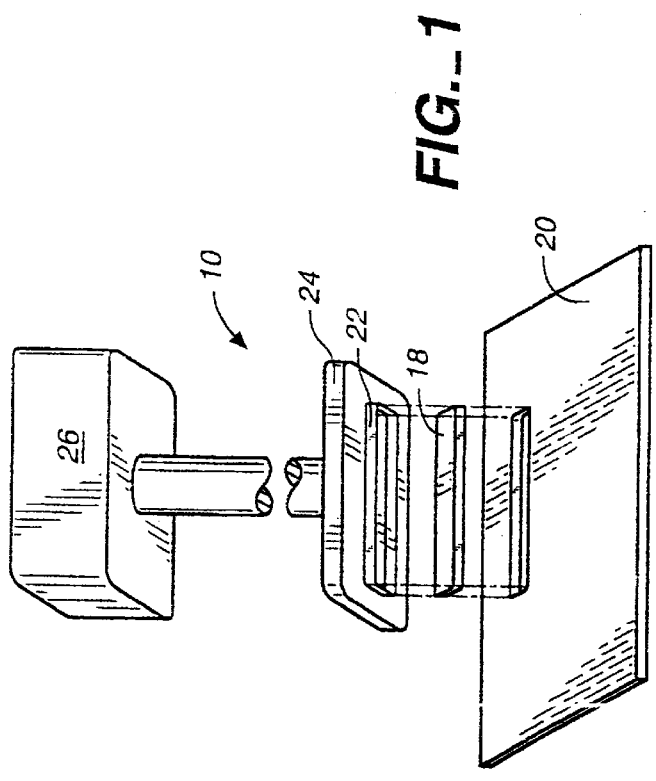
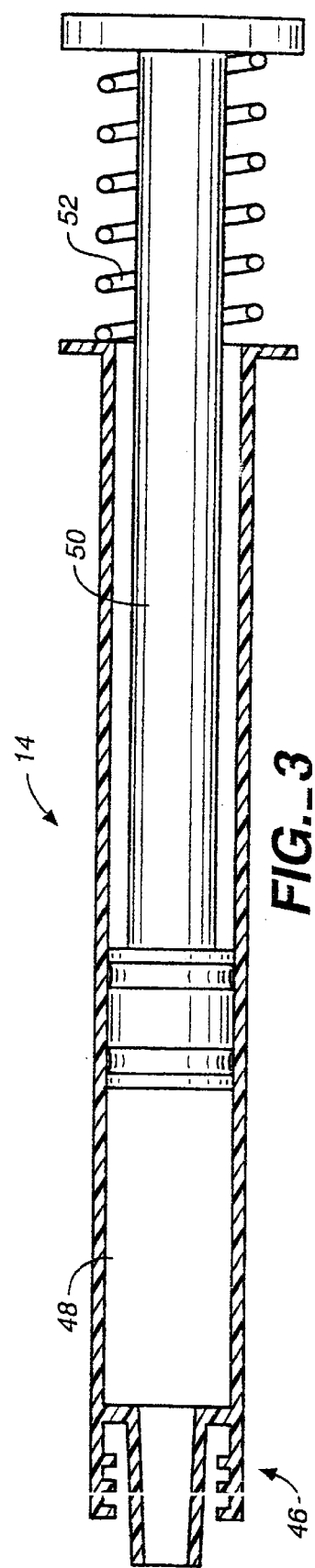

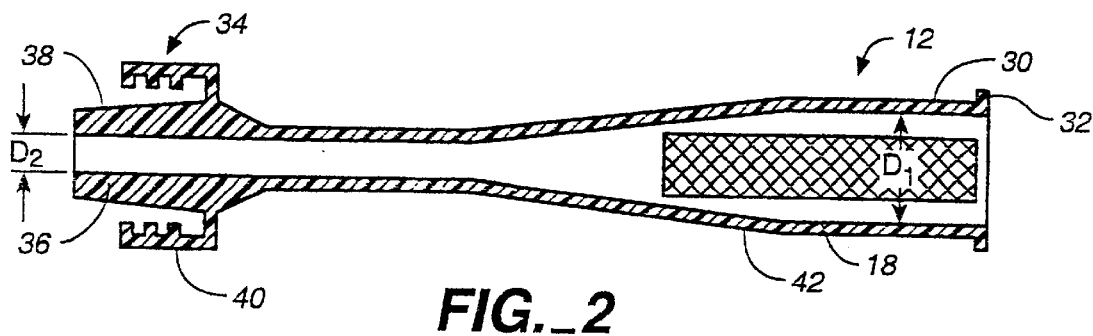
FIG._2
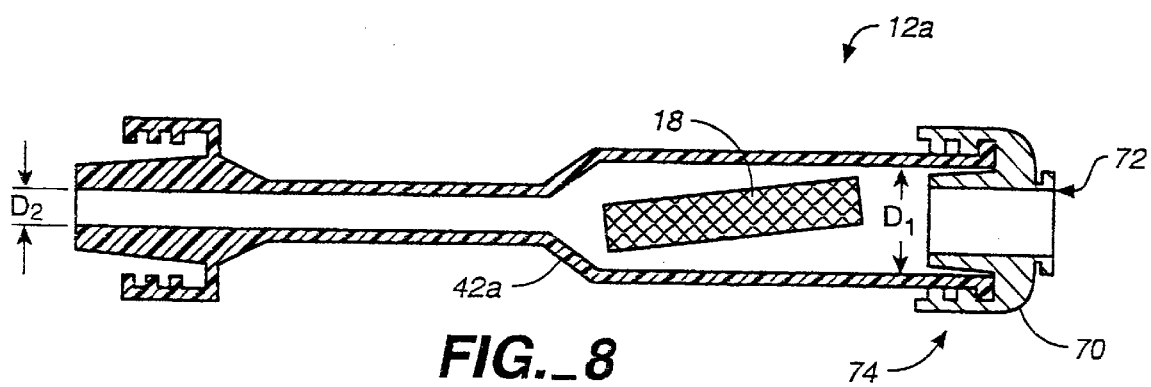
FIG._8
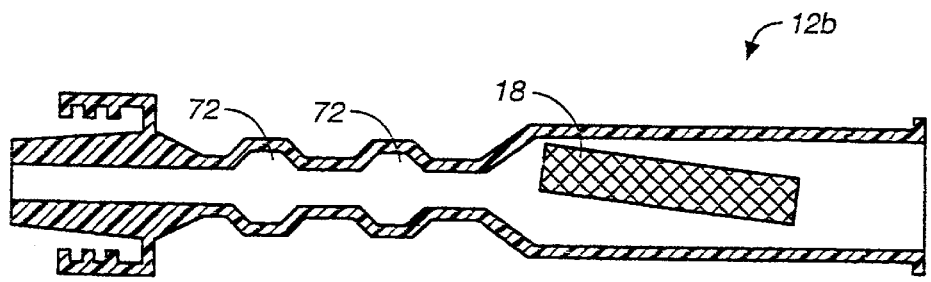
FIG._9
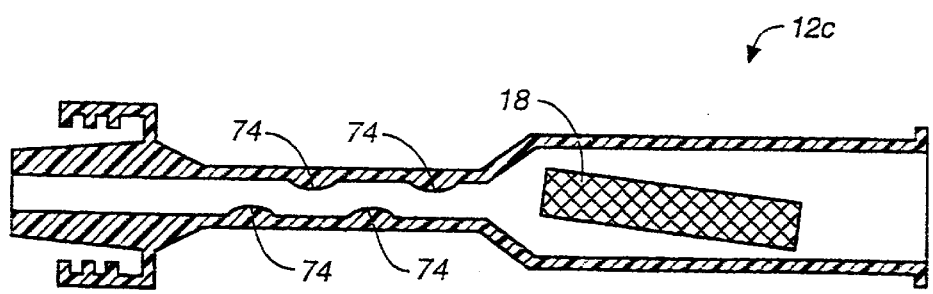
FIG._10

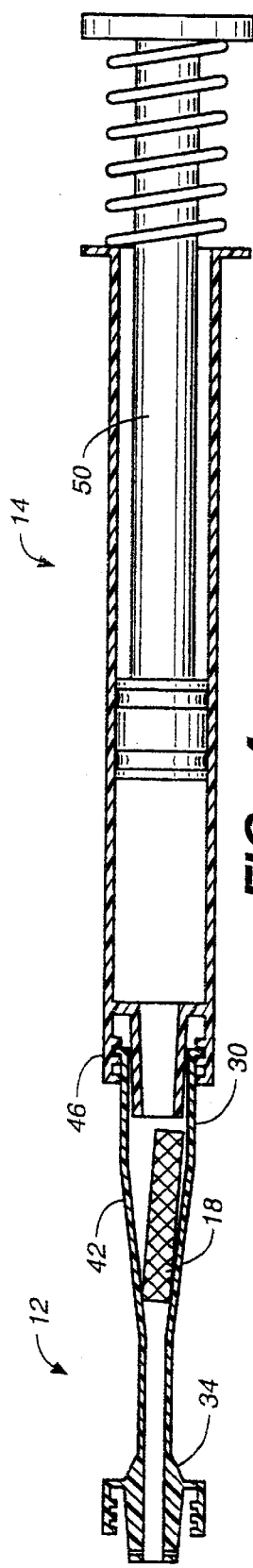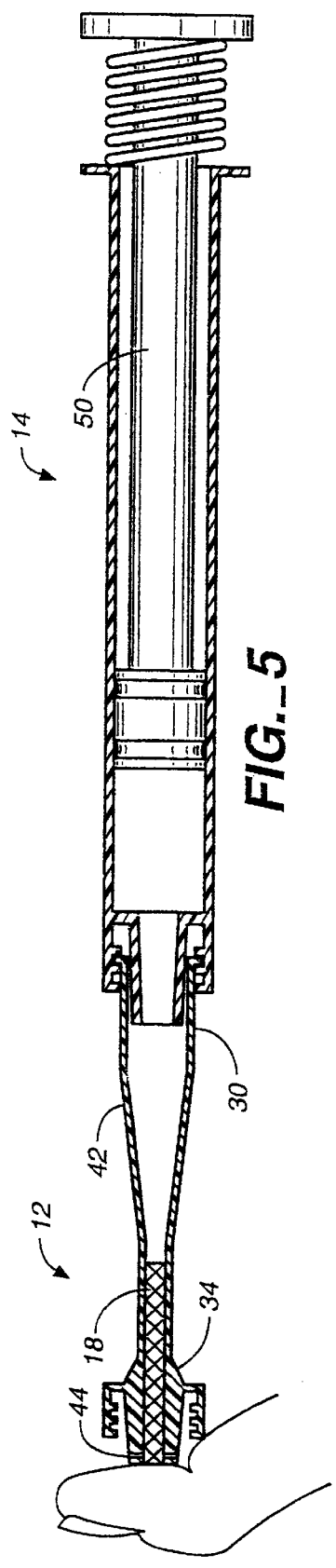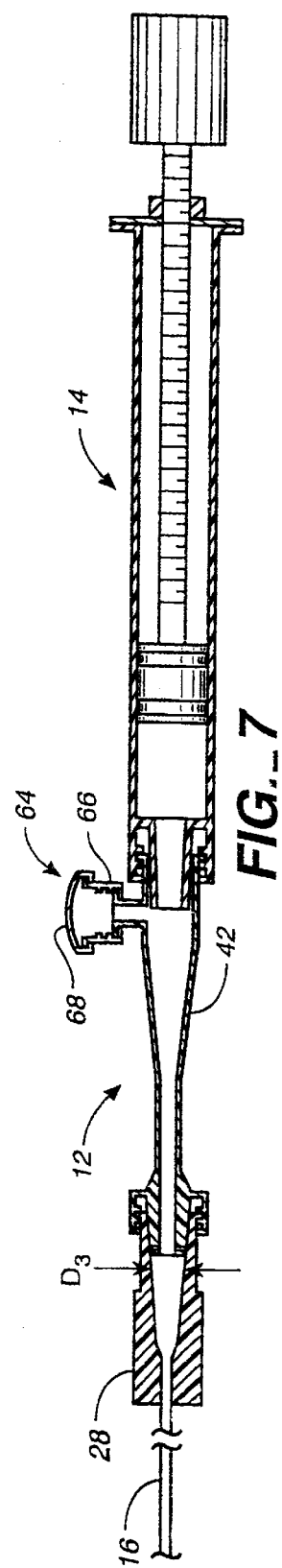

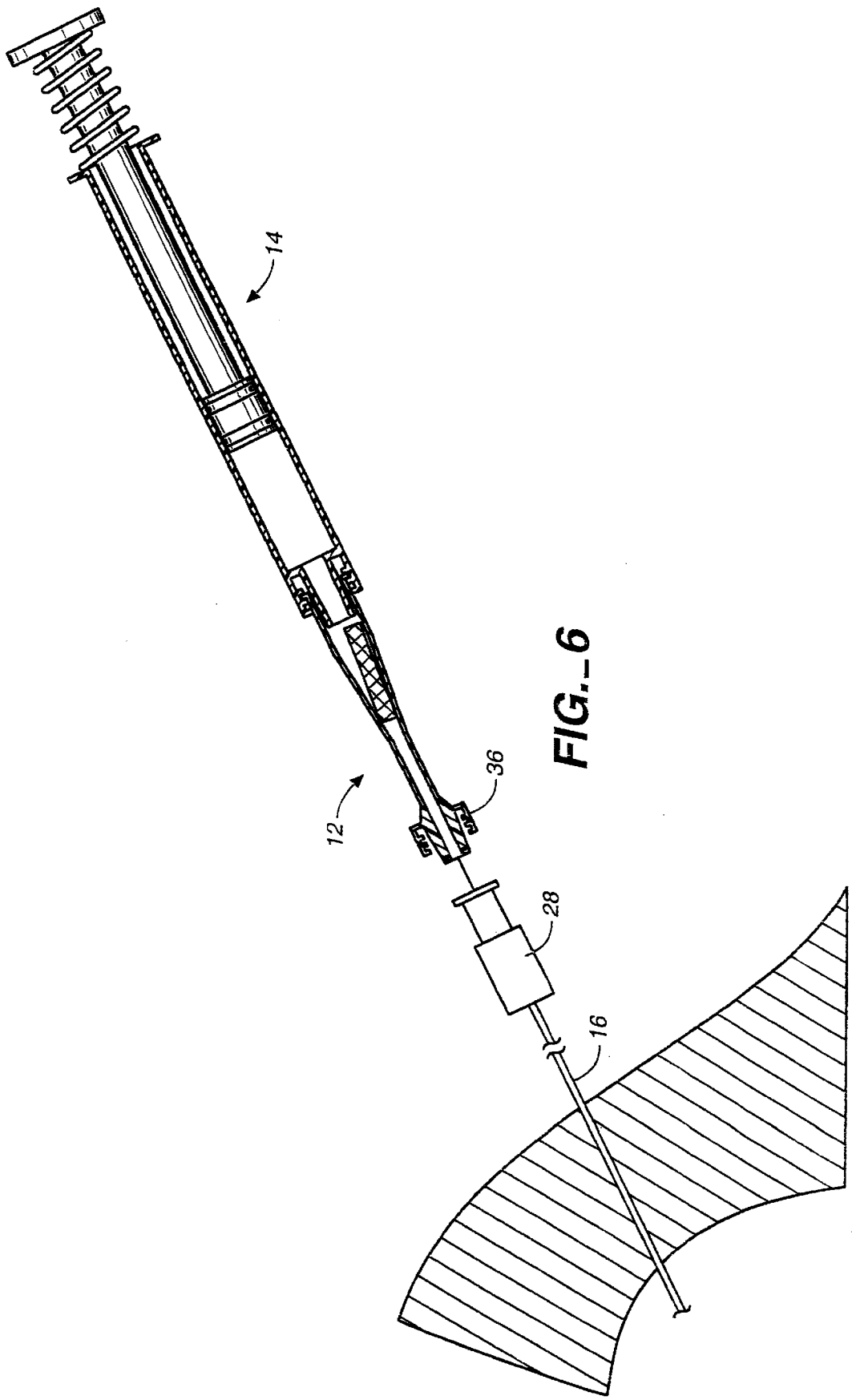
FIG._6

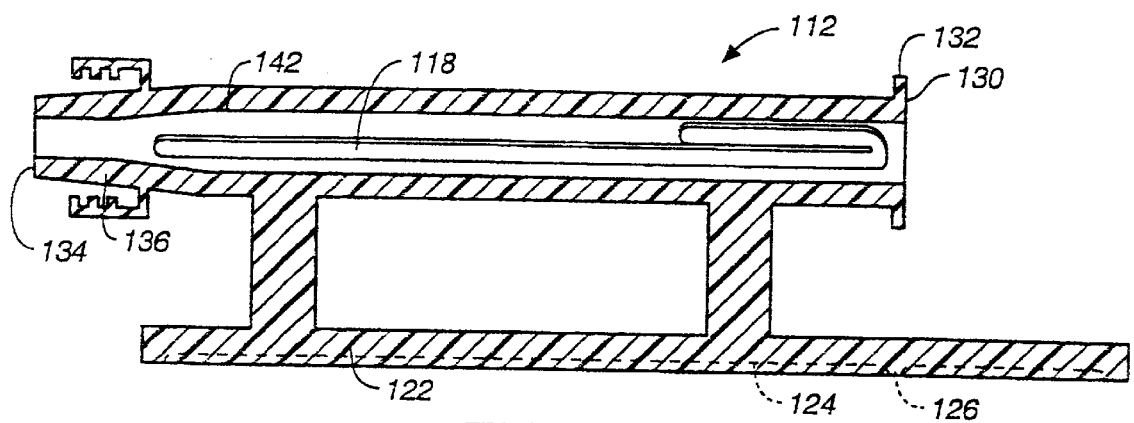
FIG._11
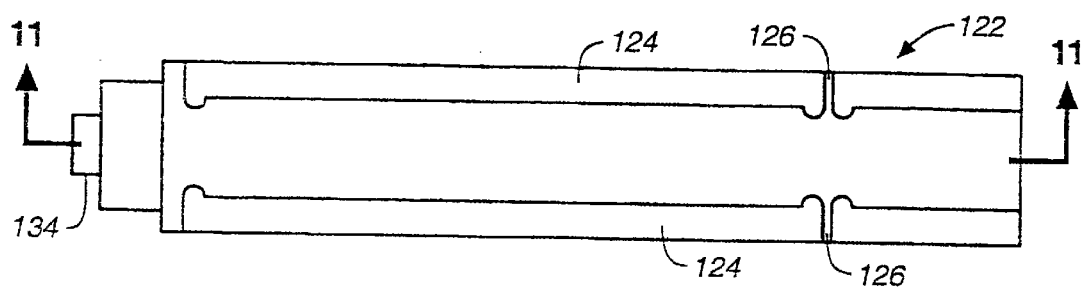
FIG._12
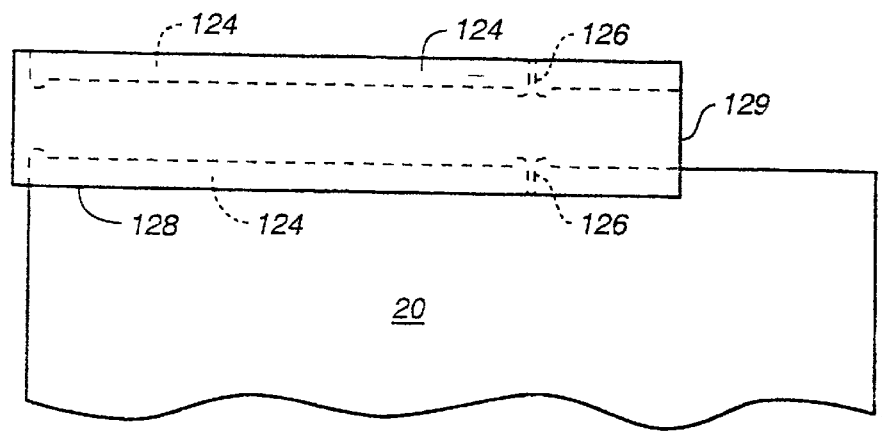
FIG._13

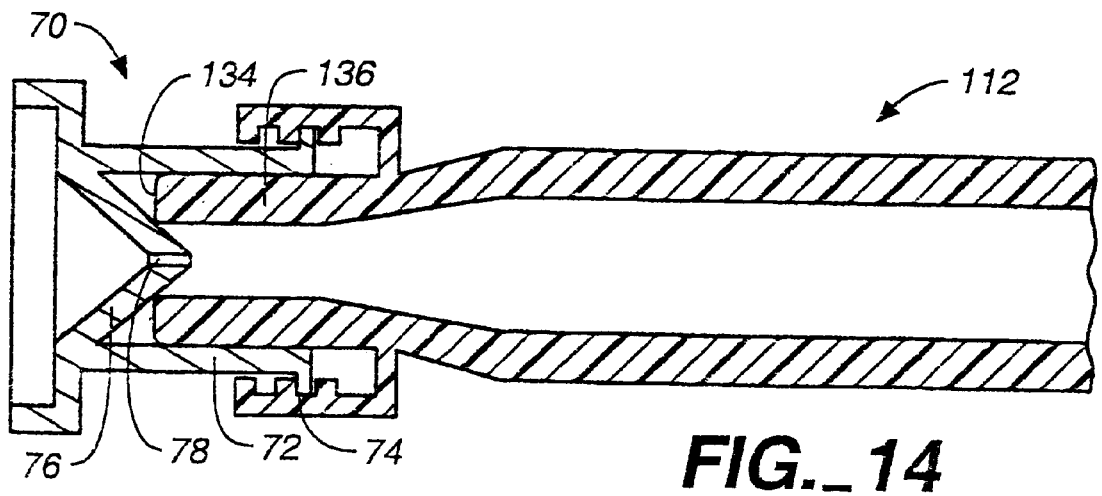
FIG._14
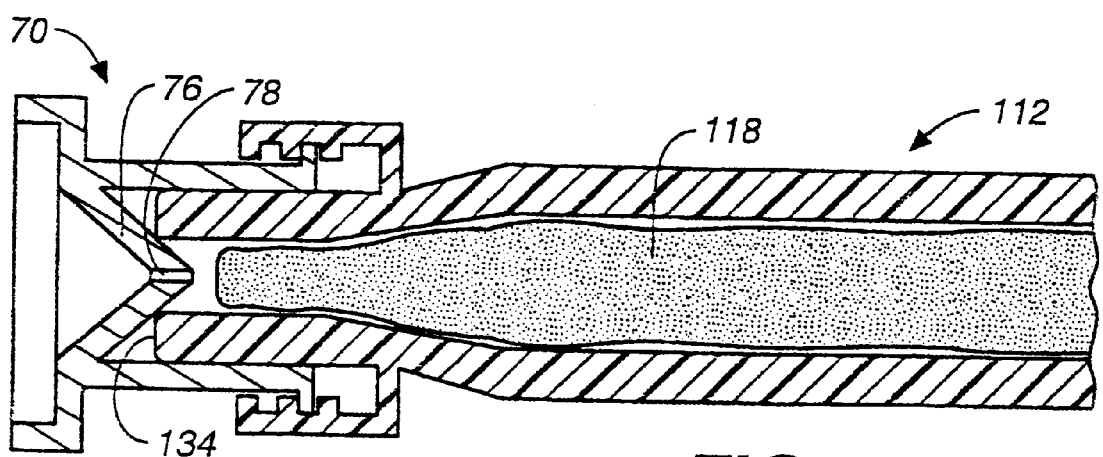
FIG._15

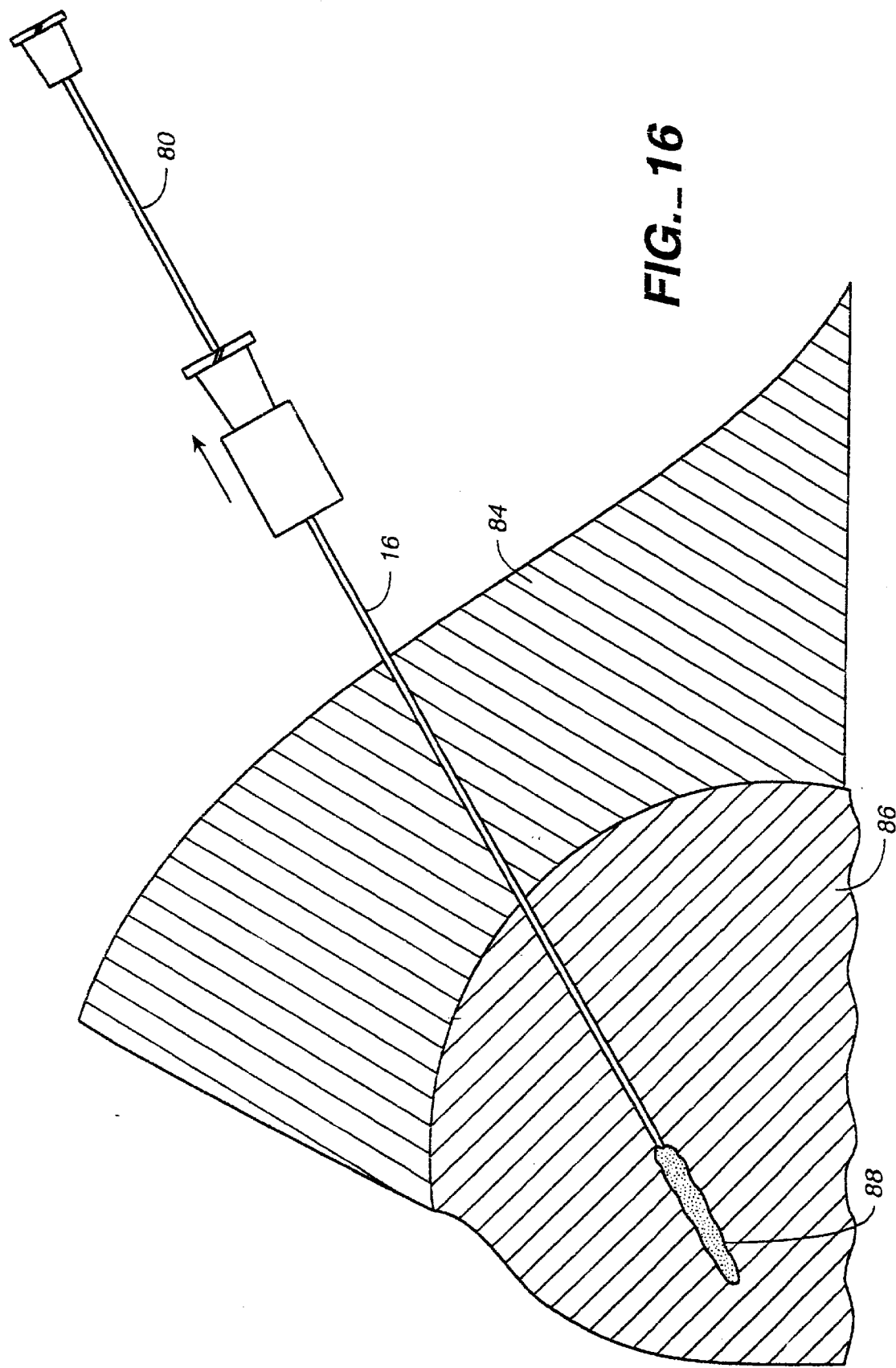
FIG._16

DEVICE AND METHOD FOR FACILITATING HEMOSTASIS OF A BIOPSY TRACT

This application is a continuation of U.S. application Ser. No. 09/613,059, filed on Jul. 10, 2000 which is a continuation of 09/247,880 filed on Feb. 10, 1999, which is a continuation-in-part of 09/071,670, filed May 1, 1998.

BACKGROUND OF THE INVENTION

1. Field of the Invention

The invention relates to a wound closure device, and more particularly, the invention relates to a device and method for facilitating hemostasis of a biopsy tract or other puncture wound by injection of an absorbable sponge.

2. Brief Description of the Related Art

Percutaneous needle biopsy of solid organs is one of the most common interventional medical procedures. Millions of percutaneous needle biopsies are performed annually in the United States and throughout the world. Percutaneous biopsy is a safe procedure which has supplanted surgical biopsy for many indications, such as skin biopsy and liver biopsy.

Possible complications of needle biopsy include bleeding at the biopsy site. The amount of bleeding is related to a number of factors including needle size, tissue sample size, patient's coagulation status, and the location of the biopsy site. Vascular organs such as the liver, a common biopsy target, may bleed significantly after needle biopsy. To minimize bleeding from a biopsy site, small-gauge needles are typically used. Small gauge needles, however, produce less satisfactory biopsy specimens but frequently are favored over larger bored needles because of their perceived safety. In order to minimize the chance of internal bleeding after biopsy, external pressure is applied and patients are often asked to lie in uncomfortable positions, such as the lateral decubitus position, for a number of hours, particularly after liver biopsy.

Sterile sponges, such as Gelfoam, are prepared in dry sterile sheets which are used as packing material during surgery for control of bleeding. The sponge sheets are left in the surgical site after surgery to stop bleeding and are absorbed by the body in 1 to 6 weeks. A number of techniques have used these absorbable sterile sponge materials to plug a biopsy tract to minimize or prevent bleeding. The absorbable sponge provides a mechanical blockage of the tract, encourages clotting, and minimizes bleeding though the biopsy tract. Despite the advantages of using absorbable sponge to plug a biopsy tract this technique has not achieved widespread use because of difficulty in preparing and delivering the sponge material into the biopsy tract.

One example of a biopsy wound closure device using an implantable sponge is described in U.S. Pat. No. 5,388,588. According to this patent, a circular sponge of an absorbable foam material is precut and inserted into a biopsy site by an applicator rod having the sponge positioned on the end. Once the sponge is implanted, the sponge absorbs blood and swells to fill the tract preventing further bleeding at the biopsy site. However, the sponge is difficult to deliver and expands slowly once delivered. In addition, this delivery method can only deliver a sponge of a limited size which provides less local compression than desired and may incompletely fill the target site. Further, bleeding may continue along sections of the biopsy tract where no sponge has been delivered.

Accordingly, it would be desirable to provide a device and method which will permit the delivery of an absorbable sponge to a biopsy tract in a simple and reliable manner.

SUMMARY OF THE INVENTION

The present invention relates to a device and method for facilitating hemostasis of a biopsy tract or other puncture wound by injecting an absorbable sponge. The system according to the present invention allows the sponge to be delivered in a hydrated state through the biopsy needle or other cannula directly into the puncture wound.

In accordance with one aspect of the present invention, a system for injecting a sponge into tissue includes a pledget of sponge having a proximal end with a larger cross sectional area than a distal end, a cannula for delivering the pledget in a hydrated state to the tissue, and an adaptor connectable to the cannula for hydrating and delivering the pledget to the cannula, the adapter having a tapered lumen with a large diameter proximal end and a small diameter distal end, wherein the small diameter distal end is connectable to the cannula.

In accordance with an additional aspect of the present invention, a method of forming a sponge pledget for delivery to tissue includes steps of cutting a strip of sponge from a sheet of sponge material and folding the strip to form a pledget with a first end having a first cross sectional area and a second folded end having a second cross sectional area which is larger than the first cross sectional area.

In accordance with a further aspect of the present invention, a system for preparing and delivering a hydrated sponge to a cannula for delivery to tissue includes an adaptor and a template. The adaptor includes an elongated member having a first end, a second end, and a lumen extending from the first end to the second end, a luer connector provided at the second end for connection to a cannula, a tapered section of the lumen tapering from a first diameter at the first end to a second diameter at the second end which is smaller than the first diameter such that a dry sponge pledget having a width larger than the second diameter is compressible when hydrated to allow passage of the pledget into the second diameter. The template is configured for use in cutting the sponge to a size to be received in the elongated member for delivery to the cannula.

In accordance with an additional aspect of the invention, an adaptor system for delivering a hydrated sponge to a cannula for delivery to tissue includes an elongated adaptor having a distal end, a proximal end, a lumen tapering from a larger diameter at a proximal end to a smaller diameter at the distal end, and a luer connection at the distal end, and a removable vent cap configured to engage the luer connection, the vent cap having a vent hole which allows fluid to pass out of the adaptor through the cap but prevents the sponge from passing through the vent hole.

In accordance with another aspect of the invention, a method of delivering a sponge into a tissue access tract includes the steps of delivering a hydrated sponge pledget through a cannula positioned in a tissue access tract at a velocity E while withdrawing the cannula from the tissue at a velocity V to deposit the sponge pledget and seal the tissue access tract, wherein the velocity E is greater than or equal to the velocity V.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a perspective view of a punch for forming pledgets;

FIG. 2 is a side cross sectional view of an adaptor for delivery of a pledget to a needle;

FIG. 3 is a side cross sectional view of a syringe for connection to the adaptor;

FIG. 4 is a side cross sectional view of an adaptor and syringe combination with a pledget positioned within the adaptor;

FIG. 5 is a side cross sectional view of an adaptor and syringe combination in accordance with an alternative embodiment in which the pledget has been hydrated and moved into a small diameter end of the adaptor;

FIG. 6 is a side cross sectional view of the loaded adaptor and syringe combination in preparation for connection to a biopsy needle;

FIG. 7 is a side cross sectional view of an alternative embodiment of an adaptor connected to a biopsy needle and syringe;

FIG. 8 is a side cross sectional view of an alternative embodiment of an adaptor;

FIG. 9 is a side cross sectional view of an alternative embodiment of an adaptor with enlargements in the lumen for kneading the pledget;

FIG. 10 is a side cross sectional view of an alternative embodiment of an adaptor with irregularities in the lumen for kneading the pledget;

FIG. 11 is a side cross sectional view of an alternative embodiment of an adaptor for delivery of a pledget including a template attached to the adaptor;

FIG. 12 is a bottom view of the adaptor and template of FIG. 11;

FIG. 13 is a top view of the template as it is used for cutting a pledget from an absorbable sponge sheet;

FIG. 14 is a side cross sectional view of a distal end of an adaptor with a vent cap attached;

FIG. 15 is a side cross sectional view of the adaptor and vent cap of FIG. 14 having a pledget staged within the adaptor; and FIG. 16 is a side cross sectional view of a portion of an organ and a system for delivering a pledget into a biopsy tract in the organ.

DETAILED DESCRIPTION OF THE PREFERRED EMBODIMENTS

The system of the present invention delivers an absorbable sponge material in a hydrated state to facilitate hemostasis of a biopsy tract or other puncture wound in a simple and safe manner. The apparatus for delivering a hydrated absorbable sponge will be described below in connection with treatment of a biopsy tract after a percutaneous needle biopsy. However, the invention may be used for facilitating hemostasis of other types of puncture wounds or tissue access tracts to prevent bleeding of these wounds.

The system for facilitating hemostasis of the biopsy tract includes a punch 10 for cutting a pledget 18 of absorbable sponge material from a sheet of this material, an adaptor 12 for delivering the pledget to a biopsy needle 16, and a syringe 14 for hydrating and injecting the pledget. The adaptor 12 allows a relatively large pledget of absorbable sponge material to be compressed and inserted into the biopsy tract in a hydrated state. The absorbable sponge material for use in facilitating hemostasis may be any absorbable sponge which is capable of deforming upon hydration to be delivered by fluid pressure through a biopsy needle or other cannula.

Prior to discussing the present invention in further detail, the following terms are defined:

"Pledget" means a piece of absorbable sponge of a generally elongated shape having a size which allows injection in a hydrated state through a biopsy needle or other cannula.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which when implanted within a human or other mammalian body is absorbed by the body.

"Hydrate" means to partially or fully saturate with a fluid, such as, saline, water, contrast agent, thrombin, therapeutic agent, or the like.

"Kneading" of the absorbable sponge material means both dry and wet manipulation of sponge material which compresses, enlarges, or changes the shape of the sponge material causing the sponge material to have improved expansion response.

FIG. 1 illustrates one example of a punch 10, also called a dye cutter, for cutting an absorbable sponge sheet 20 into pledgets 18 of an appropriate size for delivery to a biopsy tract. The punch 10 includes a rectangular blade 22 fixed to a plate 24 having a handle 26. The punch 10 is pressed down onto a flat sheet 20 of commercially available absorbable sponge to cut the pledget 18 of an appropriate size. In addition to the punch 10 illustrated in FIG. 1 other cutting devices, such as, a scissor type hand punch, an automatic punching machine, or a templet and knife may be used for preparation of the pledget 18. An alternative pledget forming system will be discussed in further detail below with respect to FIGS. 11–13.

FIG. 2 shows the adaptor 12 according to the present invention in which the pledget 18 is placed for hydration and for delivery through the biopsy needle 16. The adaptor 12 allows pieces of absorbable sponge material with relatively large cross sections to be easily delivered through a biopsy needle 16 with a much smaller cross section. The adaptor 12 also functions to remove air from the pledget 18.

The adaptor 12 which delivers the hydrated pledget 18 to the needle 16 includes a first end 30 having an annular lip 32 or female luer fitting for connection to the syringe 14. A second end 34 of the adaptor 12 has a male luer fitting 36 for connection to a biopsy needle 16 or other cannula. The luer fitting 36 includes a tapered external surface 38 and a retaining ring 40 with internal threads for receiving an annular lip of the biopsy needle. The adaptor 12 has an internal lumen with a first diameter $D_1$ at the first end 30 and a second diameter $D_2$ at the second end 34. Between the first and second ends of the adaptor 12 a tapered section 42 of the adaptor provides a funnel for compressing the hydrated pledget 18 prior to injection through the biopsy needle 16 and needle hub 28.

The adaptor 12 may be formed in any known manner such as by molding from a plastic material. Preferably, the adaptor 12 is transparent so that the pledget 18 can be viewed through the adaptor and the user can visually monitor when the pledget is loaded within the adaptor and when the pledget has been delivered into the needle. The adaptor lumen may be provided with a friction reducing coating for improved delivery. The delivery fluid also reduces friction for improved delivery by wetting the exterior surface of the pledget 18.

The syringe 14 includes a male luer fitting 46, a fluid chamber 48, and a plunger 50. The first end 30 of the adaptor 12 is connectable to the luer fitting 46 of the conventional syringe 14. The syringe 14 may be provided with a spring 52 for automatic filling of the syringe 14 with a predetermined volume of fluid. Alternatively, the syringe may include a threaded syringe plunger, as shown in FIG. 7, for accurate injection of small quantities of fluid. The syringe volume will vary depending on the amount of fluid needed for hydration and delivery of the pledget 18 through the biopsy needle 16.

A biopsy needle 16 for use with the present invention is preferably a co-axial biopsy needle, such as a bi-axial or a tri-axial biopsy needle. A co-axial biopsy needle includes an outer needle or cannula through which a tissue sample is removed with a tissue scoop or other biopsy instrument. Once the tissue sample has been removed, the outer cannula remains in the patient as illustrated in FIG. 6. Although the cannula for delivery of the sponge pledget has been described as a biopsy needle, the cannula may be a catheter, sheath, or any other type of cannula.

A preferred method of facilitating hemostasis of a biopsy tract will be described with reference to FIG. 4 which shows the loading and hydration of the pledget 18 within the adaptor 12. A pledget 18 is cut as described above and placed within the adaptor 12 from the first end 30 of the adaptor. The syringe 14 is filled with a predetermined amount of fluid, such as saline, and is connected to the first end 30 of the adaptor 12 by the luer fitting 46. The plunger 50 of the syringe 14 is then depressed slowly causing fluid to pass into the adaptor 12, hydrating the pledget 18, and filling the adaptor with a column of fluid. Care should be taken to inject the fluid slowly to prevent the pledget from being ejected out of the second end 34 of the adaptor. Preferably, the user waits a few seconds once the fluid is injected into the adaptor 12 until the pledget 18 is adequately hydrated creating a lubricous surface on the pledget. The pledget 18 may expand within the adaptor to fill or nearly fill the lumen of the adaptor. The adaptor 12 with the pledget 18 hydrated within the proximal end is ready to inject the pledget into a biopsy tract to facilitate hemostasis within the biopsy tract. The adaptor 12 may be loaded prior to beginning the biopsy procedure.

After the biopsy procedure has been completed, the outer sheath of the biopsy needle 16 through which the biopsy has been taken is maintained in place within the biopsy tract, as shown in FIG. 6. The biopsy needle 16 provides pre-established targeting of the delivery site for delivery of the absorbable sponge pledget 18 and eliminates the uncertainty of re-access. The luer fitting 36 of the adaptor 12 is connected to the biopsy needle hub 28, as illustrated in FIG. 6. The biopsy needle 16 is withdrawn a short distance, such as about 1 to 20 mm, along the biopsy tract to provide space for the pledget 18 to be received in the biopsy tract. Additional fluid is then rapidly injected by the syringe to move the pledget 18 into the biopsy needle 16. When the adaptor lumen has been blocked by the hydrated pledget 18 which has swelled within the adaptor, injection of additional fluid will push the pledget through the tapered section 42 of the adaptor. If the adaptor lumen has not been entirely blocked by the pledget 18, the venturi effect will help draw the pledget through the tapered section 42 of the adaptor. After the pledget 18 is moved to the biopsy needle 16, the pledget 18 is then delivered from the needle 16 to the biopsy tract by rapid injection of additional fluid by the syringe 14. The hydrated pledget 18 quickly expands upon delivery to fill the available space in the biopsy tract to facilitate hemostasis and provide localized compression.

As illustrated in the cross sectional view of FIG. 7, one example of a needle hub 28 has an interior diameter $D_3$ which is larger than the diameter $D_2$ at the distal end 36 of the adaptor 12. The large internal diameter needle hub 28 allows the hydrated pledget 18 which has been compressed by the tapered section 42 of the adaptor to expand in the needle hub before being compressed again into the needle lumen. This compression and enlargement of the hydrated absorbable sponge material, does not adversely effect the pledget delivery and in fact improves the expansion response of some delivered sponge materials as will be discussed in further detail below.

A smooth tapered transition between the lumen of the needle hub 28 and the needle lumen helps to provide for easy injection of the pledget 18. However, needles having internal steps between the needle hub 28 and the needle 16 have been used and the pledget 18 is still injected successfully. According to an alternative embodiment of the invention, the needle hub 28 may be designed to have a inner diameter approximately the same as the inner diameter $D_2$ at the distal end 36 of the adaptor.

Preferably, specific measured doses of fluid are used to achieve each of the steps of the treatment procedure depending on the pledget size and the dimensions of the adaptor 12, the needle 16, and the needle hub 28. The pledget 18 should be completely delivered into the biopsy tract by the fluid and only a minimal amount of extraneous fluid should be delivered. For example, the pledget 18, once inside the needle, may be delivered with about 0.02 to 1.5 ml of fluid depending on the size of the needle 16 used. Injection of larger amounts of fluid may distend the biopsy tract or displace the pledget within the organ.

According to one example, a pledget 18 having a size of approximately 20 mm by 2 mm cut from a sheet of commercially available Gelfoam having a thickness of approximately 1.5 mm can be hydrated and injected through a standard 18 gauge, approximately 15 cm long biopsy needle with approximately 0.9 ml of fluid. An adaptor according to this example has a first diameter $D_1$ of about 0.38 cm, a second diameter $D_2$ of about 0.14 cm, a total length of about 3.80 cm, and a taper angle of about 45°. About 0.3 ml of fluid is injected slowly to hydrate the pledget 18 and fill the adaptor with a column of fluid. Approximately 0.3 ml of fluid is then injected to load the pledget 18 from the adaptor 12 into the biopsy needle 16. Finally, about 0.3 ml of fluid is injected to deliver the pledget 18 into the biopsy tract. Loading of the pledget from the adaptor 12 into the needle 16 and delivery from the needle to the biopsy tract can be combined in one step by delivery of approximately 0.6 ml. Accurate and complete injection of the pledget with a minimum amount of extraneous fluid is achieved by this volumetric injection technique.

According to an alternative embodiment of the adaptor illustrated in FIG. 4, vent holes 44 extend through the side walls of the adapter 12 adjacent the second end 34 for venting fluid during loading of the pledget 18. As illustrated in FIG. 5, the user places a finger over the second end 34 of the adaptor 12 to prevent the pledget from exiting the adaptor. The plunger 50 of the syringe 14 is then depressed slowly causing fluid to pass into the adaptor 12 and hydrate the pledget. Preferably, the user waits a few seconds once the fluid is injected into the adaptor 12 until the pledget 18 is hydrated. Once the pledget 18 is hydrated, additional fluid is then injected quickly into the adaptor 12 to move the pledget 18 from the first end 30 of the adaptor towards the second end 34 of the adaptor. As the pledget 18 is compressed by the tapered section 42 of the adaptor 12 air and fluid are allowed to escape from the adaptor through the vent holes 44. Once the pledget 18 has been moved into the position illustrated in FIG. 5 adjacent the second end 34, fluid injection is halted. The adaptor 12 with the hydrated pledget 18 within the distal end is ready to insert the pledget through a biopsy needle to facilitate hemostasis within the biopsy tract.

As an alternative to placement of a finger at the distal end of the adaptor 12 during advancement of the pledget 18 through the tapered section 42, a removable cap may be used. Further, the vent holes 44 may be omitted and a screen or a cap having a screen may be used to allow fluid to pass through the screen while the screen prevents the pledget 18 from being ejected. One example of a vent cap will be described in further detail below with respect to FIGS. 14 and 15.

An alternative embodiment of the delivery system is illustrated in FIG. 7 in which an adaptor 12 is provided with a pressure indicator 64 to monitor pledget injection. Preferably, the pressure indicator 64 is removably attached at a luer fitting 66 provided on a side of the adaptor 12. The pressure indicator 64 includes a pressure dome 68 movable from the convex shaped extended position illustrated in FIG. 7 to a flat position depending on the pressure inside the adaptor 12. Internal pressure within the biopsy needle 16, the adaptor 12, and the syringe 14 will drop as the pledget 18 is extruded from the biopsy needle into the biopsy tract. This causes the pressure dome 68 to move from the convex position illustrated in FIG. 7 to a flat position, indicating that pledget delivery is complete.

FIG. 8 illustrates an alternative embodiment of an adaptor 12a in which the tapered section 42a is shorter and more abrupt. The particular size and shape of the adaptor 12a according to either FIG. 2 or FIG. 8 may vary depending on the size of biopsy needle, the tissue sample size, and the size of pledget to be delivered. One example of the adaptor 12a of FIG. 8 for delivery of an absorbable sponge pledget 18 through an approximately 18 gauge biopsy needle has a first adaptor diameter $D_1$ of about 0.25 cm or greater, preferably about 0.30 to 0.80 cm and a second adaptor diameter $D_2$ of about 0.25 cm or less, preferably, about 0.05 to 0.23 cm. An angle made by a wall of the tapered section 42a with a longitudinal axis of the adaptor 12a may vary from about 5° to 90°, but is preferably between about 30° and 60°. The tapered section 42a is illustrated with a substantially planar interior surface, when shown in cross section. However, the tapered section 42a may also have a convex or concave surface in cross section. The dimensions described for the adaptor 12a are appropriate for use with an approximately 18 gauge biopsy needle commonly used for liver biopsies. For some of the much larger biopsy needles or cannulas used for skin or breast biopsies the adaptor dimensions would be scaled up accordingly.

FIG. 8 also shows a connector 70 for connecting the adaptor 12 to a syringe 14 when the proximal end of the adaptor is larger in diameter than the standard syringe fitting. The connector 70 includes a first end 72 for connection to the syringe 14 and a second end 74 for connection to the adaptor 12.

One type of absorbable sponge material which is acceptable for use in the present invention is Gelfoam, manufactured by the Upjohn Company. Gelfoam is a porous, pliable, cross-linked gelatin material and is available commercially in sheet form as pre-compressed or non-compressed sponge. The material may be provided preformed as a pledget 18 or may be cut with a punch 10, or a stencil or template and knife to form a pledget as described above. Once hydrated, the pledget 18 can be easily compressed to fit into a lumen having a smaller cross sectional area than the original cross sectional area of the pledget. Additionally, the kneading of the hydrated pledget 18 during delivery encourages air trapped within the Gelfoam to be expelled and replaced with fluid, allowing rapid expansion upon delivery. When a pledget 18 of a pre-compressed Gelfoam is hydrated and kneaded (expelling air) during delivery, the pledget will have the absorbtion capacity to rapidly expand to many times (e.g., 3 or more times) its original dry volume upon delivery. When a pledget 18 of the non-compressed Gelfoam is hydrated and kneaded (expelling air) during delivery, the pledget will have the absorbtion capacity to rapidly expand to its original dry volume upon delivery. These properties make the Gelfoam sponge material particularly useful for facilitating hemostasis of biopsy sites.

Abrupt lumen diameter changes within or between the adaptor 12 or the needle 16 will improve "kneading" of the absorbable sponge material improving hydration of the absorbable sponge material thereby improving the expansion properties of the hydrated delivered absorbable sponge. According to the alternative embodiments of the adaptor illustrated in FIGS. 9 and 10, enlarged, recessed, or irregular areas in the lumen of the adaptor are provided to impart additional kneading action to the absorbable sponge material further improving expansion properties of the sponge.

The adaptor 12b of FIG. 9 includes two enlarged areas 72 of the lumen. As the absorbable sponge pledget 18 passes through the lumen of the adaptor 12b the material expands and is compressed by the adaptor to increase kneading of the pledget. FIG. 10 illustrates another alternative embodiment of the adaptor 12c including a lumen with a plurality of staggered irregularities 74 for improved kneading of the absorbable sponge pledget 18. The irregularities 74 will preferably have a relatively smooth surface to prevent the absorbable sponge material from becoming caught on the irregularities.

FIG. 11 illustrates an alternative embodiment of an adaptor 112 with a pledget formation template 122 attached to the adaptor. As shown in FIG. 11, the adaptor 112 includes a proximal end 130 having a female luer 132 and a distal end 134 having a male luer 136. The pledget 118 is inserted in the proximal end 130. A tapered section 142 is provided within the adaptor 112 for compressing the pledget 118 into the biopsy needle.

When delivering a pledget 118 of absorbable sponge material, it is important to deliver a desired amount of the sponge material using a minimum amount of fluid. Some devices and methods which allow the delivery of sponge material with a minimum amount of fluid include the use of the pledget configuration illustrated in FIG. 11, the use of a vent cap for staging of the pledget as illustrated in FIGS. 14 and 15, and the withdrawal of the biopsy needle during delivery as illustrated in FIG. 16.

Pledgets 118 having increased proximal cross sectional areas are more easily delivered than pledgets with constant cross sectional areas or decreased proximal cross sectional areas. FIG. 11 illustrates a pledget 118 having a proximal cross sectional area which is approximately twice its distal cross sectional area. The smaller material mass at the distal end of the pledget 188 increases the ease of inserting the pledget into the adaptor 112. The smaller distal end of the pledget also passes through the delivery cannula or biopsy needle without creating a large back pressure to resist the delivery of the pledget through the cannula. The larger proximal section of the pledget 118 provides a better seal within the interior of the adaptor 112 and the cannula 16 which allows a minimum amount of fluid to be used to advance the pledget. The increased material at the proximal end of the pledget 118 also increases the amount of sponge material delivered to the biopsy tract.

Pledgets 118 with increased cross sectional area proximal ends may be prepared in a variety of manners. For example, if a pledget 118 is prepared from a sheet of sponge material, the increased proximal mass can be achieved by cutting the pledget with an enlarged proximal end. Alternatively, the pledget 118 may be formed by folding, rolling, compressing, or otherwise manipulating the sponge material to the desired shape. The proximal pledget mass may also be increased by adding separate pieces of material to the proximal end of the pledget. This additional material may be layered, wrapped, coiled or attached to the pledget in any other manner. The pledgets may also be formed by molding, bump extruding, dipping, or the like. The larger cross sectional area proximal end is generally about 1.2 to 4 times the cross sectional area of the distal end. In addition, the proximal end with the larger cross section area preferably extends along about ⅛ to ¾ of the total pledget length.

The pledget 118 illustrated in FIG. 11 has been formed by cutting a strip of material from an absorbable sponge sheet 20 with the aid of the template 122 as illustrated in FIG. 13. After the strip is cut, the proximal end of the strip is then folded back onto itself to form a pledget 118 with an increased cross sectional area and material mass at a proximal end. One example of a preferred embodiment of a Gelfoam pledget for delivery down a 20 gauge biopsy needle or cannula has a size of approximately 0.1×1.5×0.06 inches and is folded as illustrated in FIG. 11 to an overall length of about 0.9 inches. Placing this pledget 118 in an adaptor 112 having a largest internal diameter of 0.125 inches allows the pledget to be delivered to a 20 gauge or larger biopsy needle. Other common biopsy procedures use an 18 gauge or larger biopsy needle through a slightly larger guide cannula and would receive a somewhat larger pledget. After taking a core sample and removing the biopsy needle from the cannula guide, a pledget 118 maybe delivered through the cannula to the biopsy site. The pledget 118 for use in the system employing an 18 gauge or larger biopsy needle may be formed from a strip which is approximately 0.11–0.12 inches wide by about 3.125 inches long with a thickness of about 0.06 inches and folded to an overall length of about 2.2 inches. This pledget having a single thickness distal end and double thickness proximal end can De delivered from an adaptor having a largest internal diameter of approximately 0.125 inches.

One method for forming the pledget 118 with the enlarged proximal end with the aid of a template 122 is illustrated in FIG. 13. The template 122 is a flat plate having recesses 124 along one or more edges of the template. The recesses 124 have a width and a length which corresponds to a preferred width and length of the pledget. The recesses 124 form a raised bar 126 at a location where the pledget should be folded. When the template is pressed onto a sheet 20 of absorbable sponge material, the bar 126 makes an indentation or groove in the sponge material. A user cuts along the side 128 and end 129 edges of the template 122 with a blade to form a strip of the sponge material which is then folded along the groove or crease formed by the bar 126 to form the pledget 118. It is important to securely hold the sponge sheet by applying downward pressure to the template 122 during cutting to prevent tearing and breaking of the sponge material. Prior to folding the strip of sponge material to form the pledget, the strip may be compressed with a flat surface of the template to compact the sponge and assist in loading the pledget into the adaptor 112.

Although the template 122 has been illustrated as a plate which is attached to the adaptor 112, it should be understood that the template can also be a separate member. In addition, the template 122 may provide guides for forming pledgets of different sizes for delivery through different sized biopsy needles. The template 122 may be provided with or without the creasing bar 126 and may be transparent or opaque. In the opaque version, the edges of the recesses 124 are used to align the template with an edge of the sponge sheet 20. In contrast, in a transparent version of the template, the recesses 124 may be eliminated and a visual indication or line may be provided which assists in aligning an edge of the sponge sheet with the template.

FIGS. 14 and 15 illustrate a preferred vent cap 70 for use with the adapter 112. As discussed above with respect to FIG. 5, vents maybe used to assist in hydrating and staging the pledget within the adapter. In particular, vents will allow the pledget to be moved to a preferred axial location within the adapter 112 prior to delivery. In addition, the vents allow fluid to be injected and air to be removed from the pledget prior to delivery. The vent cap 70 as illustrated in FIG. 14 includes a female luer connector 72 including a flange 74 which is received on the male luer 136 of the adapter 112. The vent cap 70 also includes a conical portion 76 which is configured to extend into a distal end 134 of the adaptor 112. The conical portion 76 has one or more fluid paths or vent holes 78 which allow air and fluid to exit through the vent cap but prevent the absorbable sponge material of the pledget 118 from passing through the vent cap. The vent hole may alternatively be positioned between the vent cap 70 and the adapter 112. Preferably, an exterior of the conical portion 76 forms a seal with the lumen of the adaptor 112 at the distal end. The diameter of the vent hole 78 is approximately 0.005–0.02 inches, preferably approximately 0.01 inches. This small vent hole 78 allows the purging and venting of fluid and air from the adapter 112 but does not allow the pledget 118 to pass through the venthole, even at high pressures such as 5 psi or greater. The use of the vent cap 70 allows the user to apply high pressures with the syringe used to hydrate the pledget The high pressures drive the fluid into the pledget causing rapid and thorough hydration of the sponge material. Repeated pulsing of the fluid with the syringe will provide more complete hydration of the pledget.

The vent cap 70 also positions the pledget 118 at a preferred axial position just proximal to the distal end 134 of the adapter 112 as illustrated in FIG. 15. This positioning of the pledget 118 away from the end of the adaptor prevents the pledget from becoming trapped between the adaptor 112 and the biopsy needle hub 28 which is attached to the distal end of the adaptor. In addition, after hydration of the pledget and removal of the vent cap 70 the sponge material may tend to swell out of the distal end of the adapter 112. Accordingly, the conical portion 76 of the vent cap 70 preferably extends into the adaptor 112 approximately 0.01 to 0.1 inches, more preferably about 0.01 to 0.03 inches.

According to the present invention, the portion of the vent cap 70 which extends into the lumen of the adaptor 112 can be any desired shape such as dome-shaped, cylindrical, conical or other shape.

As described above, the pledget maybe delivered to the biopsy tract by holding the biopsy needle or cannula 16 stationary and injecting the pledget through the biopsy needle. If additional pledgets are to be delivered, the biopsy needle 16 is withdrawn a distance sufficient to accommodate an additional pledget and the additional pledget is then injected.

According to an alternative embodiment of the invention, the method of delivering the pledget into the biopsy tract may include withdrawing the biopsy needle or cannula 16 during delivery of the pledget 18 to deliver the pledget in an elongated trail which follows the biopsy tract. Placing the absorbable sponge material in a tril which fills the entire biopsy tract provides the added benefit of providing hemostasis along the entire biopsy tract. This is particularly helpful for stopping the bleeding of biopsy tracts in organs which tend to have excessive bleeding such as the liver, kidney, spleen, and other vascular organs.

In order to achieve a trail of absorbable sponge material in the biopsy tract, one method of the present invention involves the delivery of the pledget into the biopsy needle by a predetermined amount of fluid. The biopsy needle is then withdrawn at a velocity V while the pledget material is ejected from the biopsy needle at a velocity E with respect to the biopsy needle. The velocity V at which the biopsy needle is withdrawn is equal to or less than the velocity E at which the absorbable sponge material is delivered. The control of injection of fluid and withdrawal of the needle to achieve the desired trail of absorbable sponge material in the biopsy tract maybe controlled with an injection controlling device.

According to an alternative embodiment of the invention illustrated in FIG. 16, the adaptor maybe used to deliver the pledget into the biopsy needle 16 and then the adaptor is removed from the biopsy needle. A plunger or stylet 80 which is generally provided with the biopsy needle 16 for inserting the biopsy needle is then used to deliver the pledget from the biopsy needle. As shown in FIG. 16, the biopsy needle extends through the tissue 84 and into the organ 86 for removal of a core of tissue. After biopsy, the pledget is injected into the needle 16 and the plunger 80 is placed within the biopsy needle so that a distal end of the plunger abuts the proximal end of the pledget 118. The plunger 80 is then held stationary while the biopsy needle 16 is withdrawn from the biopsy site. The plunger 80 causes the pledget 118 to be delivered in a trail 88 which fills the biopsy tract. The trail 88 preferably extends along the entire biopsy tract to or past a surface of the organ 86. The delivery of the trail 88 of absorbable sponge material provides an advantage over the delivery of discrete blobs of material because the trail is able to provide hemostasis along the entire tract. In contrast, if a blob of absorbable sponge material is delivered within the tract at a depth of 1–2 cm from the surface of the organs, this 1–2 cm of biopsy tract may continue to bleed significantly.

As an alternative to delivery of the pledget as a trail, the pledget may be delivered as a plug. To deliver a plug the plunger 80 is advanced into the needle 16 pushing the pledget out of the distal end of the needle while the needle is held stationary. A combination of delivery of plugs and trails may also be used. The pledget material may be delivered entirely within a single anatomical structure or may cross two or more anatomical structures such as an organ, surrounding tissue and facial layer.

Although the invention is primarily intended for delivery of absorbable sponge, non-absorbable sponge may also be delivered with the devices, systems, and methods of the present invention. A non-absorbable sponge may be desirable where it will be necessary to locate the biopsy site or tract after the procedure.

Although the pledget 18 has been shown and described as having a rectangular cross section, pledgets of other shapes may also be used. For example, the pledget may be preformed in any shape, such as with a rectangular or circular cross section or may be rolled from a thin sheet of absorbable sponge material. The pledget 18 may have a multi-sided cross section, a star shaped cross section, or a folded cross section and may have through or blind holes formed in the dry pledget. In addition, the pledget size and shape can be matched to the size and shape of a particular delivery site. Pledget shapes having greater surface area provided by features such as fins provide faster hydration.

The continuous structure of the absorbable sponge pledget 18 provides more secure and reliable placement than a paste or liquid and can even facilitate partial withdrawal, removal, or movement of the delivered pledget.

In some instances it may be desirable to deliver multiple pledgets in spaced apart positions along the biopsy tract, particularly for a long biopsy tract. For delivery of additional pledgets, the biopsy needle 16 is retracted a distance sufficient to provide a space to accommodate an additional pledget 18 and the injection procedure described above is repeated for the additional pledget(s). For a particularly large biopsy site or cavity, additional pledgets 18 may be injected beside an initially injected pledget until the cavity is filled.

Although biopsy is most commonly performed by biopsy needle, biopsy may also be performed through other cannulas, such as catheters, long needles, endoscopes, or the like. The treatment procedure according to the present invention can be used for facilitating hemostasis of puncture wounds through different types of cannulas including needles, catheters, endoscopes, and the like. In addition, the treatment procedure and systems according to the present invention may be used to deliver absorbable or non-absorbable sponge for other therapys. For example, sponge may be delivered for cosmetic or reconstructive bulking or for temporary or permanent intravascular embolization.

The absorbable sponge pledget 18 may be used to deliver a beneficial agent, such as contrast agent, thrombin, radiation treatment, or the like. The pledget can also be used to deliver therapeutic agents, such as radioactive isotopes for localized treatment of tumors, anti-cancer agents, anti-metastatic agents, and the like. Examples of anti-cancer agents include 5-fluorouracil, cisplatin, prednisone, and others described in U.S. Pat. No. 4,619,913 which is incorporated herein by reference. The absorbable sponge pledget 18 may be presoaked with the beneficial agent for delivery to the biopsy tract. Alternatively, the pledget 18 may be hydrated with the beneficial liquid agent or the agent may be delivered to the pledget after the pledget is placed within the biopsy tract.

A pledget formed of commercially available Gelfoam material will be absorbed by the body within 1 to 6 weeks. However, the pledget material may be designed to provide different rates of absorption. For example, Gelfoam can be designed to be absorbed at different rates by varying the degree of cross-inking. Preferably, the pledget is designed to be absorbed in less than one month.

The treatment of a biopsy tract with a hydrated and injected pledget 18 of absorbable sponge to facilitate hemostasis provides substantial advantages in comfort over external pressure methods. In addition, the present invention also provides advantages over the insertion of an absorbable sponge material in a dry state with an applicator. In particular, the adaptor 12 allows a relatively large pledget to be compressed and inserted into the biopsy tract in a hydrated state. The injected pledget 18 conforms in shape quickly to the shape of the biopsy tract and immediately begins blocking blood flow. In contrast, a dry piece of sponge material must be cut to the particular size of the biopsy tract and does not swell to fill the tract until the blood has sufficiently saturated the sponge material which can take significantly longer and provides inadequate local compression.

While the invention has been described in detail with reference to the preferred embodiments thereof, it will be apparent to one skilled in the art that various changes and modifications can be made and equivalents employed, without departing from the present invention.

What is claimed is:

1. A method of preparing a sponge pledget for delivery to a body to facilitate hemostasis, the method comprising:

positioning a sponge pledget in an adaptor;

covering a distal end of the adaptor with a vent cap which allows for venting fluid and prevents expulsion of the pledget; and hydrating the sponge by injecting fluid into the adaptor.

2. The method of claim 1, wherein the pledget is positioned in an adaptor which is substantially tubular.

3. The method of claim 1, wherein the vent cap positions a distal end of the sponge at a predetermined longitudinal position with respect to the adaptor.

4. The method of claim 3, wherein the predetermined longitudinal position is proximal of the distal end of the adaptor.

5. The method of claim 1, wherein the vent cap includes a conical portion configured to extend into the distal end of the adaptor.

6. The method of claim 5, wherein the vent hole is provided at a tip of the conical portion.

7. The method of claim 1, further comprising delivering the hydrated sponge pledget from the adaptor by removing the vent cap from the distal end of the adaptor and injecting additional fluid into the adaptor to deliver the pledget.

8. The method of claim 1, wherein the sponge is hydrated by injecting fluid at pressures of at least 5 psi.

9. The method of claim 1, wherein the sponge is hydrated by pulsing the injected fluid to provide complete hydration.

10. The method of claim 1, wherein the sponge is positioned in the adaptor in a dry state.

11. A method of preparing a sponge pledget for delivery to a body to facilitate hemostasis, the method comprising:

positioning a sponge pledget in an adaptor;

covering a distal end of the adaptor with a vent cap which allows for venting fluid and prevents expulsion of the pledget; and moving the sponge pledget distally in the adaptor to a predetermined position by injecting fluid into the adaptor.

12. The method of claim 11, wherein the pledget is positioned in an adaptor which is substantially tubular.

13. The method of claim 11, wherein the predetermined position is proximal of the distal end of the adaptor.

14. The method of claim 11, wherein the vent cap includes a conical portion configured to extend into the distal end of the adaptor.

15. The method of claim 14, wherein the vent hole is provided at a tip of the conical portion.

16. The method of claim 11, further comprising delivering the sponge pledget from the adaptor by removing the vent cap from the distal end of the adaptor and injecting additional fluid into the adaptor to deliver the pledget.

17. The method of claim 11, wherein the sponge is positioned by injecting fluid at pressures of at least 5 psi.

18. The method of claim 11, wherein the sponge is positioned in the adaptor in a dry state.

* * * * *